(12) United States Patent
Gürtler et al.

(10) Patent No.: US 8,987,446 B2
(45) Date of Patent: Mar. 24, 2015

(54) BIMETALLIC COMPLEXES AND THE USE THEREOF IN PRODUCING DIARYL CARBONATE

(75) Inventors: Christoph Gürtler, Köln (DE); Thomas Ernst Müller, München (DE); Pieter Ooms, Krefeld (DE); Johann Rechner, Kempen (DE); Friedhelm Risse, Köln (DE); Angelina Prokofieva, Leverkusen (DE); Franco Doro, Aachen (DE); Burkhard Köhler, Zierenberg (DE); Walter Leitner, Aachen (DE); Aurel Wolf, Wülfrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/515,710

(22) PCT Filed: Dec. 9, 2010

(86) PCT No.: PCT/EP2010/069323
§ 371 (c)(1),
(2), (4) Date: Sep. 25, 2012

(87) PCT Pub. No.: WO2011/073087
PCT Pub. Date: Jun. 23, 2011

(65) Prior Publication Data
US 2013/0018186 A1 Jan. 17, 2013

(30) Foreign Application Priority Data
Dec. 14, 2009 (DE) .......................... 10 2009 058 053

(51) Int. Cl.
*C07D 241/46* (2006.01)
*C07F 15/00* (2006.01)
*C07C 68/00* (2006.01)

(52) U.S. Cl.
CPC ........... *C07F 15/0066* (2013.01); *C07C 68/005* (2013.01)

USPC .......................................................... 544/342

(58) Field of Classification Search
USPC .................................................. 544/338, 342
See application file for complete search history.

(56) References Cited

U.S. PATENT DOCUMENTS

| 4,201,721 A | 5/1980 | Hallgren |
| 4,349,485 A | 9/1982 | Hallgren |
| 5,231,210 A | 7/1993 | Joyce et al. |
| 5,498,742 A | 3/1996 | Buysch et al. |
| 5,760,272 A | 6/1998 | Pressman et al. |

FOREIGN PATENT DOCUMENTS

| DE | 2738437 A1 | 4/1978 |
| EP | 0667336 A1 | 8/1995 |
| EP | 0858991 A1 | 8/1998 |
| WO | WO-2008054024 A1 | 5/2008 |

OTHER PUBLICATIONS

International Search Report for PCT/EP2010/069323 mailed Feb. 22, 2011.

*Primary Examiner* — James O Wilson
*Assistant Examiner* — Cecilia M Jaisle
(74) *Attorney, Agent, or Firm* — Drinker Biddle & Reath LLP

(57) ABSTRACT

The invention relates to bimetallic complexes in which the ligand contains a salophen unit which complexes copper, manganese or cobalt and a phenanthroline unit which complexes palladium and the two systems are linked by a continuous conjugated system. The invention further relates to the use of these bimetallic complexes as catalysts for the oxidative carbonylation of aromatic hydroxy compounds to form diaryl carbonates, a process for preparing diaryl carbonates using the bimetallic complex as catalyst and also diaryl carbonates prepared by oxidative carbonylation of aromatic hydroxy compounds using the bimetallic complexes of the invention as catalysts.

2 Claims, 3 Drawing Sheets

[PdPhenpzSalCu]

BIMETALLIC COMPLEXES AND THE USE THEREOF IN PRODUCING DIARYL CARBONATE

RELATED APPLICATIONS

This application is a national stage application (under 35 U.S.C. §371) of PCT/EP2010/069323, filed Dec. 9, 2010, which claims benefit of German Patent Application No. 10 2009 058 053.0, filed Dec. 14, 2009.

The invention relates to bimetallic complexes in which the ligand contains a salophen unit which complexes copper, manganese or cobalt and a phenanthroline unit which complexes palladium and the two systems are linked by a continuous conjugated system. The invention further relates to the use of these bimetallic complexes as catalysts for the oxidative carbonylation of aromatic hydroxy compounds to form diaryl carbonates, a process for preparing diaryl carbonates using the bimetallic complex as catalyst and also diaryl carbonates prepared by oxidative carbonylation of aromatic hydroxy compounds using the bimetallic complexes of the invention as catalysts.

Diaryl carbonates are suitable for the preparation of polycarbonates by the melt transesterification process (see, for example, in Chemistry and Physics of Polycarbonates, Polymer Reviews, H. Schnell, Vol. 9, John Wiley and Sons, Inc., 1964), for the production of phenylurethanes or as intermediates for active compounds in the pharmaceutical and crop protection sector.

It is known that diaryl carbonates can be obtained by phase interface phosgenation (Schotten-Baumann reaction) of aromatic hydroxy compounds. However, this process has considerable disadvantages such as the use of phosgene and solvents such as methylene chloride.

Diaryl carbonates can also be prepared by oxidative direct carbonylation of aromatic hydroxy compounds in the presence of CO, $O_2$ and a noble metal catalyst (see, for example, DE-A 27 38 437, U.S. Pat. No. 4,349,485, U.S. Pat. No. 5,231,210, EP-A 667 336, EP-A 858 991, U.S. Pat. No. 5,760,272). As noble metal, preference is given to using palladium. In addition, a cocatalyst (e.g. manganese or cobalt salts), a base, bromide sources, quaternary salts, various quinones or hydroquinones and desiccants can be used. The reaction can be carried out in a solvent such as chlorobenzene.

In the known prior art, for example J. Mol. Cat. A: Chem. 2000, 151, 37-45, copper salts, manganese salts or cobalt salts are used in an excess relative to the noble metal catalyst, as a result of which the catalyst and the cocatalyst can be utilized only with a low efficiency.

In addition, the known processes do not have a satisfactory catalyst operating life. In particular, deposition of metallic palladium occurs.

In the light of the known prior art, there was therefore a need for catalysts which make it possible for the reaction to be carried out without use of additional amounts of copper salts, manganese salts or cobalt salts as cocatalyst and make an increased efficiency of the catalyst (e.g. turnover number, TON) possible. In addition, there was a need to provide catalysts which have an increased stability.

The problem addressed has surprisingly been solved by a bimetallic complex in which the second metal is incorporated stoichiometrically relative to palladium in the complex. This compound leads to the cocatalyst being able to be utilized in a synergistic manner and to the operating life of the bimetallic catalyst being increased relative to the comparative system.

We have found bimetallic catalysts in which the catalytically active palladium and the redox-active cocatalyst are combined in one molecule and accelerated reoxidation of the palladium is made possible thereby, leading to a synergistic effect.

Bimetallic complexes of the formula (1) are described in WO 2008/054024 as photosensitizers for photovoltaic cells:

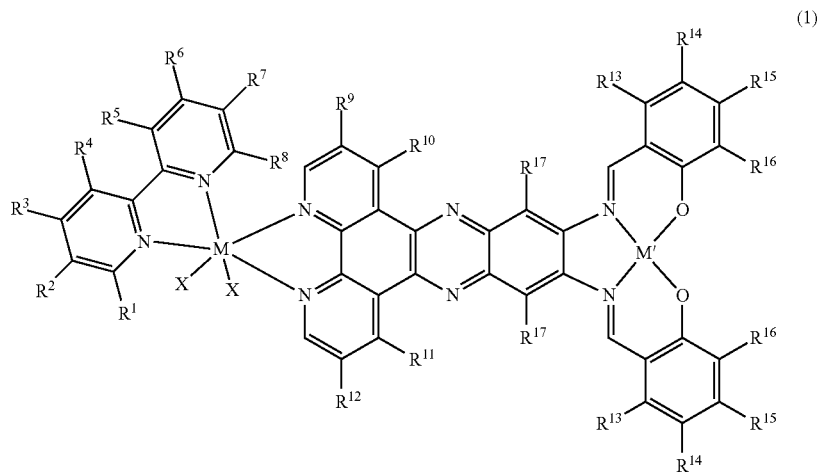

(1)

where M=Ru, Os, Fe, Re, Rh and M'=Ni, Co, Zn, Mn, Pt, Pd. The metal bound to the phenanthroline unit is in addition necessarily complexed by further bipyridine ligands. These complexes are unsuitable as catalysts for oxidative carbonylations, e.g. the preparation of diphenyl carbonate from phenol, carbon monoxide and oxygen, since the blocking of the coordination site on the metal center M by the bipyridine unit results the coordination sites no longer being available for the attachment of reactants. As catalytically active metal for oxidative carbonylations (metal center M), preference is given to palladium which is located in a coordination sphere consisting of two cis ligands and two weakly coordinated ligands (J. Mol. Cat. A: Chem. 2000, 151, 37-45).

The synthesis of such ligands and complexes is also described in European Journal of Inorganic Chemistry 2003, 10, 1900-1910. Here, two strategies are employed: formation commencing from the phenanthroline unit and complexation only after complete synthesis of the ligand and formation commencing from the salophen unit, with a template process in which the synthesis is carried out in the presence of the central ion, Ni(II), being selected. This requires, as intermediate, the 3,4-dinitrosalophen-Ni(II) complex, formula (2), whose synthesis is described in Dalton Transactions 2009, 10, 1792-1800 and the references cited therein.

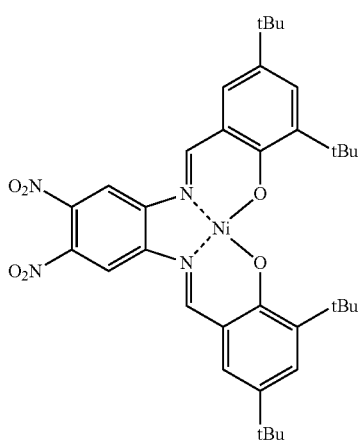

(2)

For particular applications, particularly in catalysis, complexes whose metal ions in the phenanthroline unit are not complexed by further bipyridine ligands are desired. Furthermore, the template route is simpler to carry out but has not yet been described for copper as central atom.

It has now been found that ligands which additionally contain a phenanthroline unit which can be reacted with palladium halide complexes to form bimetallic complexes in which the palladium is not stabilized by further bipyridine ligands can be prepared from 3,4-dinitrosalophen-Cu(II) complexes. It was to be expected that the palladium will be coordinated by two phenanthroline ligands since the two monodentate ligands Hal are more easily replaced than bipyridine chelates. However, the formation of palladium-bisphenanthroline complexes did not occur.

The invention accordingly provides complexes of the general formula (3),

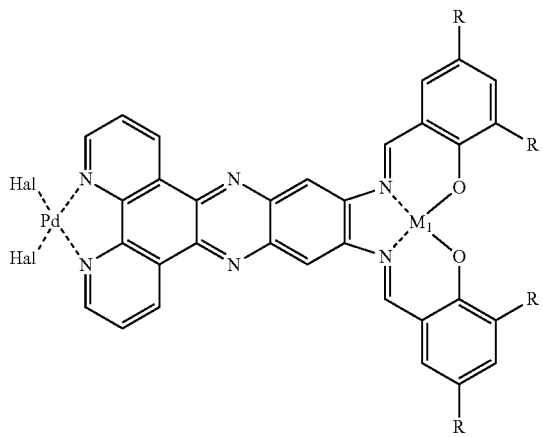

(3)

where
R is hydrogen, fluorine, chlorine, a nitro group or a $C_1$-$C_{22}$-alkyl radical, preferably methyl, isopropyl or tert-butyl, very particularly preferably tert-butyl, or a $C_6$-$C_{22}$-aryl radical, preferably phenyl, tolyl, 2-(1,4-dihydroxy)phenyl, Hal is chloride, bromide or iodide, preferably chloride or bromide, very particularly preferably bromide, or an alkoxide, for example phenoxide or methoxide, or a weakly coordinating anion such as triflate, tosylate, mesylate, tetrafluoroborate, perchlorate and hexafluorophosphate and $M_1$ is copper, manganese or cobalt.

The invention further provides complexes of the general formulae 4a and 4b which occur as intermediates in the preparation of the bimetallic complex of the invention,

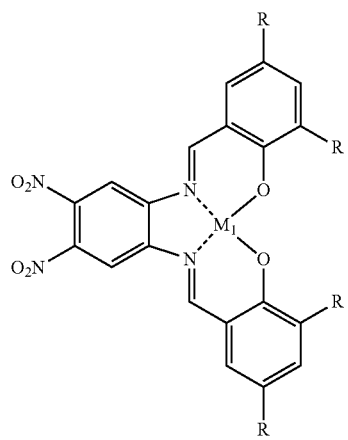

(4a)

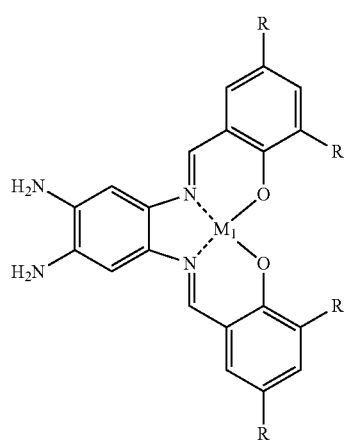

(4b)

where R and $M_1$ are as defined above.

The invention also provides for the use of the bimetallic complexes of the formula 3 as catalysts for the oxidative carbonylation of aromatic hydroxy compounds to form diaryl carbonates and also diaryl carbonates prepared by oxidative carbonylation of aromatic hydroxy compounds using complexes of the formula 3 as catalysts.

The synthesis of compounds of the formula 3 is carried out by hydrogenation of the nitro groups of the compound of the formula 4a to form compounds of the formula 4b, subsequent reaction with phendione of the formula 5

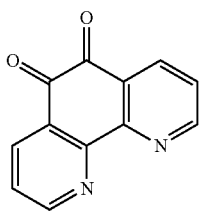

(5)

to form ligands of the formula 6

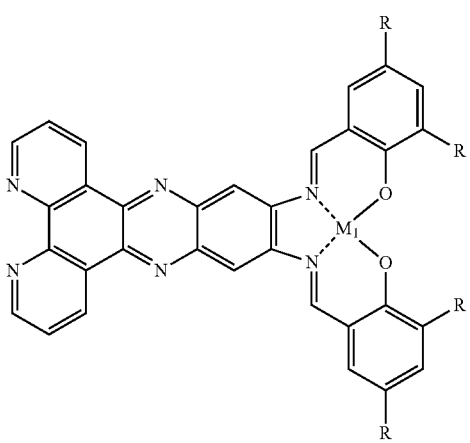

(6)

and complexation with a compound of the formula 7,

PdHal$_2$L$_2$ (7)

where Hal is as defined above and L is a ligand which is optionally present, e.g. acetonitrile, triarylphosphines, cyclooctadiene, or norbornadiene.

Figure 1:
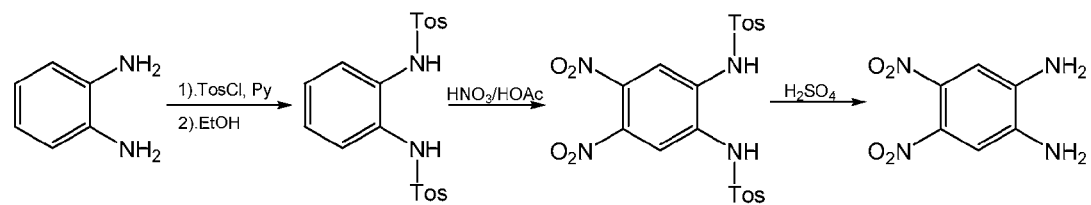
FIG. 1. Shows a reaction scheme for the preparation of 4,5-Dinitro-o-phenylenediamine according to the prior art.

The 4,5-dinitro-o-phenylenediamine required for the preparation of the complexes of the formula 4a can, for example, be prepared according to the literature reference Cheeseman G. W. H., J. Chem. Soc., 1962, 1170. The hydrogenation to form compounds of the formula 4b is carried out by hydrogenation of the compounds of the formula 4a by means of hydrogen-donating reagents such as H$_2$, hydrazine, cyclohexene or formic acid in the presence of catalysts comprising the metals Ni, Co, Pd, Pt, Ru or Rh, which may be immobilized on supports such as carbon or inorganic substances.

The reaction with phendione is carried out, for example, by joint heating under reflux with equimolar amounts of compounds of the formula 4b in solvents such as methanol, ethanol or isopropanol, chloroform, benzene, toluene or mixtures thereof, with the water formed being optionally able to be removed by azeotropic distillation.

The formation of the complexes of the formula 3 is carried out by reaction of the ligands of the formula 6 with compounds of the formula 7 in solvents such as methylene chloride, chloroform, 1,2-dichloroethane, benzene, chlorobenzene, DMF, diethyl ether, methyl tert-butyl ether or THF at temperatures of from 10° C. to the boiling point of the solvent under atmospheric pressure.

The bimetallic complexes of the invention having the formula 3 are suitable for the catalysis of the oxidative carbonylation of aromatic hydroxy compounds to form diaryl carbonates.

Aromatic hydroxy compounds for the process of the invention are those of the formula 8

Ar—OH (8), where

Ar is phenyl, naphthyl, anthryl, phenanthryl, indanyl, tetrahydronaphthyl or the radical of a 5- or 6-membered aromatic heterocycle having 1 or 2 heteroatoms from the group consisting of N, O and S, where these isocyclic and heterocyclic radicals may be substituted by 1 or 2 substituents such as straight-chain or branched C$_1$-C$_4$-alkyl, straight-chain or branched C$_1$-C$_4$-alkoxy, straight-chain or branched C$_1$-C$_4$-alkoxycarbonyl, each of which may be substituted by phenyl, cyano and halogen (e.g. F, Cl, Br), and the heterocyclic radicals may also be bound to a fused-on benzene ring.

Examples of aromatic hydroxy compounds of the formula 8 are: phenol, o-, m- and p-cresol, o-, w- and p-isopropylphenol, the corresponding halophenols and alkoxyphenols, e.g. p-chlorophenol or p-methoxyphenol, methyl salicylate, ethyl salicylate, also monohydroxy compounds of naphthalene, anthracene and phenanthrene, also 4-hydroxypyridine and hydroxyquinolines. Preference is given to using phenol and optionally substituted phenols, very particularly preferably phenol.

The preparation of a diaryl carbonate by oxidative carbonylation is carried out by reacting an aromatic hydroxy compound with carbon monoxide and oxygen in the presence of a catalyst according to the invention having the formula 3.

The oxidative carbonylation of aromatic hydroxy compounds by means of the catalysts of the invention having the formula 3 is carried out in the liquid phase in the presence or absence of solvents such as chlorobenzene, dichlorobenzene, toluene, xylene, DMF, dimethylacetamide, tetrahydrofuran, NMP, ethylene carbonate or propylene carbonate at temperatures of from 25 to 150° C., preferably from 60 to 110° C., in the presence of carbon monoxide/oxygen mixtures in a partial pressure ratio of from 1:1 to 99:1, preferably from 98:2 to 60:40, optionally in the presence of further inert gases such as nitrogen, argon or carbon dioxide, where the partial pressure ratio of inert gases to active gases is from 98:2 to 2:98, preferably from 95:5 to 50:50, and the total pressure is from 1 bar to 100 bar, preferably from 5 bar to 20 bar.

Furthermore, it is possible for other redox-active substances such as quinones, alkali metal iodides or alkaline earth metal iodides, manganese compounds, cobalt compounds, or copper compounds to be present in a weight ratio of palladium compound to redox-active substance of from 1:1 to 1:100, preferably from 1:2 to 1:20. Examples of quinones are benzoquinone, naphthoquinone and anthraquinone and substitution products thereof. Examples of manganese compounds, cobalt compounds or copper compounds are oxides, halides, acetylacetonates or carboxylates thereof.

As further cocatalysts or auxiliaries, it is possible to use onium salts such as ammonium, phosphonium or sulfonium salts, lead compounds such as lead alkyls or oxides, polymers such as polyvinylpyrrolidone, alkyl halides such as dibromoethane, in a weight ratio of palladium compound to cocatalyst or auxiliary of from 1:1 to 1:200, preferably from 1:10 to 1:50. Particular preference is given to using the bromides of the ammonium or phosphonium compounds in a weight ratio of palladium compound to auxiliary of from 1:1 to 1:200, preferably from 1:10 to 1:50.

The diaryl carbonates prepared using the complexes of the invention having the formula 3 as catalysts can be used for preparing polycarbonates or isocyanates.

The following examples illustrate the invention without restricting its scope.

EXAMPLES 4,5-Dinitro-o-phenylenediamine was prepared according to FIG. 1 of the literature reference Cheeseman G. W. H., J. Chem. Soc., 1962, 1170.

Example 1

Figure 2:
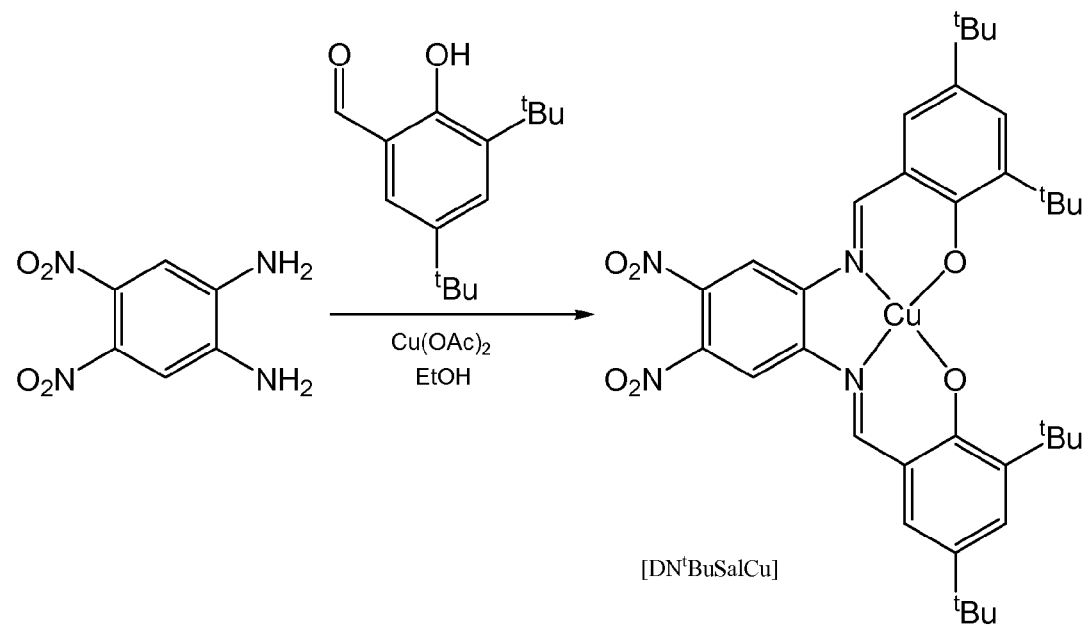
FIG. 2. Shows a reaction scheme for the preparation of [DN$^t$BuSalCu] according to the invention.

Preparation of [DN$^t$BuSalCu] (according to the invention corresponding to formula 4a) as per FIG. 2.

A solution of 0.69 g (3.48 mmol) of $Cu(OAc)_2 \cdot H_2O$ in 20 ml of ethanol was added to a mixture of 0.68 g (3.48 mmol) of 4,5-dinitro-o-phenylenediamine and 1.63 g (6.96 mmol) of 3,5-di-tert-butyl-salicylaldehyde in 80 ml of ethanol. The mixture was refluxed for 80 minutes. The precipitate was subsequently filtered off, washed with n-hexane and dried under reduced pressure.

Yield: 1.27 g (50%).

Field desorption mass spectroscopy (FD-MS, D+toluene) m/e (%): 691 (100) ($C_{36}H_{44}CuN_4O_6$)

Example 2

Figure 3:
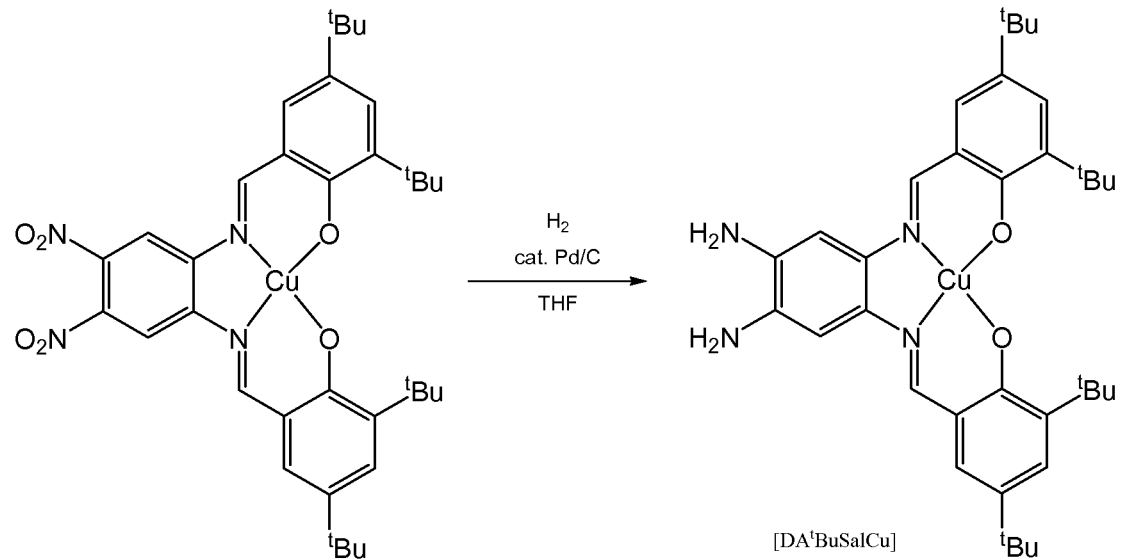
FIG. 3. Shows a reaction scheme for the preparation of [DA$^t$BuSalCu] according to the invention.

Preparation of [DA$^t$BuSalCu] (according to the invention corresponding to formula 4b) as per FIG. 3.

A suspension of 1.27 g (1.83 mmol) of [DN$^t$BuSalCu] and 0.2 g of Pd/C (10%) in 100 ml of THF was treated with a hydrogen pressure of 40 bar in a 250 ml autoclave, stirred at room temperature for 12 hours and subsequently filtered. The filtrate was evaporated under reduced pressure, the residue was washed with hexane and subsequently dried under reduced pressure.

Yield: 1.16 g (100%)

FD-MS (D+toluene) m/e (%): 631 (100) ($C_{36}H_{48}CuN_4O_2$)

Example 3

Figure 4:
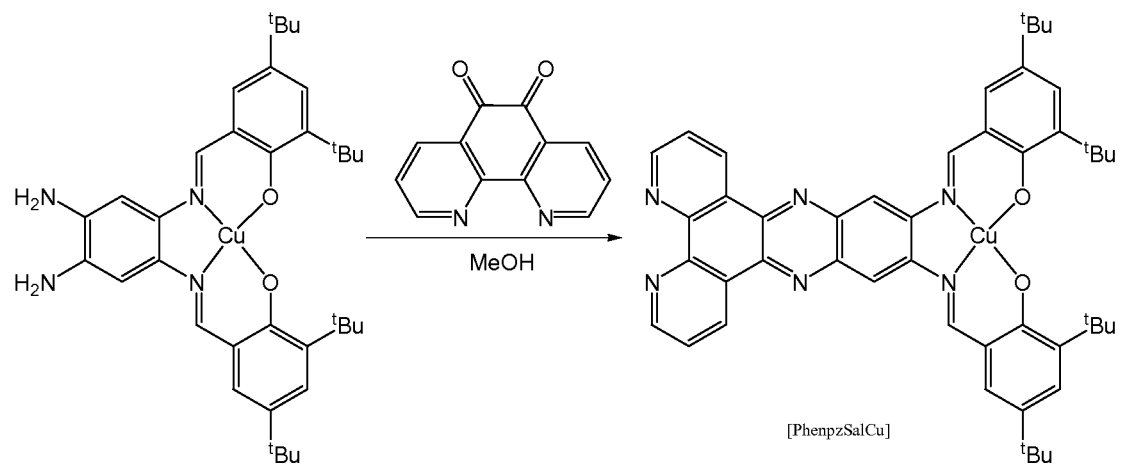
FIG. 4. Shows a reaction scheme for the preparation of [PhenpzSalCu] according to the invention.

Preparation of [PhenpzSalCu] (according to the invention corresponding to formula 6) as per FIG. 4.

A suspension of 0.5 g (0.79 mmol) of [DA$^t$BuSalCu] in 30 ml of methanol was added dropwise to a solution of 0.16 g (0.79 mmol) of phendione in 20 ml of methanol. The mixture was then refluxed for 2 hours, resulting in formation of a red precipitate which was filtered off, washed with petroleum ether and dried under reduced pressure.

Yield: 0.5 g (78%)

FD-MS (D+toluene) m/e (%): 805 (100) ($C_{48}H_{50}CuN_6O_2$)

Example 4

Figure 5:
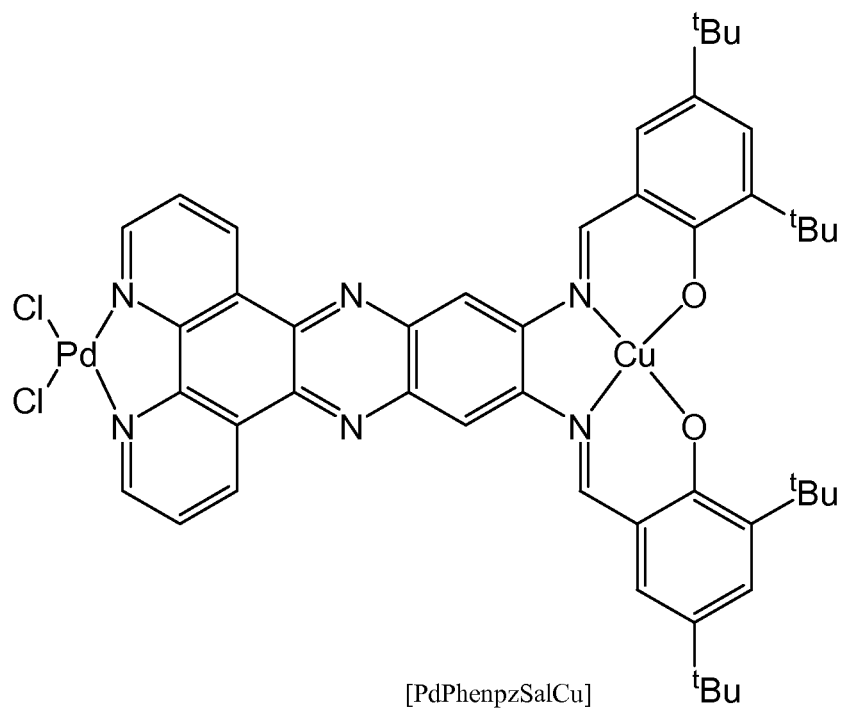
FIG. 5. Shows the chemical structure of [PdPhenpzSalCu] according to the invention.

Preparation of [PdPhenpzSalCu] (according to the invention corresponding to formula 1) as per FIG. 5.

The solution of 0.01 g (0.06 mmol) of [$Pd(CH_3CN)_2Cl_2$] was added to a solution of 0.05 g (0.06 mmol) of [PhenpzSalCu] in 5 ml of methylene chloride and the mixture was stirred at room temperature for 16 hours. The volatile constituents were taken off under reduced pressure and the residue was admixed with hexane. The precipitated product was then filtered off and dried under reduced pressure.

Yield: 0.025 g (42%)

FD-MS (D+toluene) m/e (%): 981 (10) ($C_{48}H_{50}Cl_2CuN_6O_2Pd$), 805 (100) ($C_{48}H_{50}CuN_6O_2$)

Example 5

Use of [PdPhenpzSalCu] as catalyst for preparing diphenyl carbonate

A mixture of 894 mg (9.5 mmol) of phenol, 8.5 mg (0.0086 mmol) of [PdPhenpzSalCu], 32 mg (0.29 mmol) of benzoquinone, 222 mg (0.69 mmol) of tetrabutylammonium bromide and 110 mg of molecular sieves (3 Å) was flushed three times with 10 bar of a mixture of 97% of CO and 3% of $O_2$ and was then treated with 18 bar of this gas mixture. The mixture was then heated to 90° C. while stirring at 900 rpm. Analysis of the reaction mixture by gas chromatography after a reaction time of 3 h gave a yield of 5.1 mg (0.024 mmol) of diphenyl carbonate corresponding to a TON of the catalyst based on palladium of 2.8 and based on copper of 2.8.

Example 6

A mixture of 954 mg (10.1 mmol) of phenol, 9.1 mg (0.0093 mmol) of [PdPhenpzSalCu], 43.8 mg (0.39 mmol) of benzoquinone, 212 mg (0.66 mmol) of tetrabutylammonium bromide and 110 mg of molecular sieves (3 Å) was flushed three times with 10 bar of a mixture of 97% of CO and 3% of $O_2$ and then treated with 18 bar of this gas mixture. The mixture was then heated to 90° C. while stirring at 900 rpm. Analysis of the reaction mixture by gas chromatography after a reaction time of 14 hours gave a yield of 5.8 mg (0.027 mmol) of diphenyl carbonate corresponding to a TON of the catalyst based on palladium of 3.0 and based on copper of 3.0.

The TONs based on palladium and copper increase with reaction time when using the compound according to the invention.

Comparative Example 7

Reworking of the procedure in literature reference J. Mol. Cat. A: Chem. 2000, 151, 37-45.

A mixture of 920 mg (9.78 mmol) of phenol, 4.6 mg (0.012 mmol) of [$Pd(Phen)Cl_2$], 20 mg (0.056 mmol) of [$Co(acac)_3$], 31.8 mg (0.29 mmol) of benzoquinone, 219 mg (0.66 mmol) of tetrabutylammonium bromide and 110 mg of molecular sieves (3 Å) was flushed three times with 10 bar of a mixture of 97% of CO and 3% of $O_2$ and then treated with 18 bar of this gas mixture. The mixture was then heated to 90° C. while stirring at 900 rpm. Analysis of the reaction mixture by gas chromatography after a reaction time of 3 hours gave a yield of 5.8 mg (0.027 mmol) of diphenyl carbonate corresponding to a TON of the catalyst based on palladium of 3.4 and based on cobalt of 0.5.

Comparative Example 8

A mixture of 994 mg (10.6 mmol) of phenol, 4.3 mg (0.011 mmol) of [$Pd(Phen)Cl_2$], 18.2 mg (0.050 mmol) of [$Co(acac)_3$], 36.2 mg (0.33 mmol) of benzoquinone, 203 mg (0.60 mmol) of tetrabutylammonium bromide and 110 mg of molecular sieves (3 Å) was flushed three times with 10 bar of a mixture of 97% of CO and 3% of $O_2$ and then treated with 18 bar of this gas mixture. The mixture was then heated to 90° C. while stirring at 900 rpm. Analysis of the reaction mixture by gas chromatography after a reaction time of 14 hours gave a yield of 4.7 mg (0.022 mmol) of diphenyl carbonate corresponding to a TON of the catalyst based on palladium of 2.7 and based on cobalt of 0.4.

In the comparative examples, the addition of a cobalt salt as cocatalyst in addition to the palladium catalyst is necessary. The molar ratio of palladium to cocatalyst is 1:6.5, while when using the bimetallic complex as per examples 5 and 6 the ratio is 1:1.

TABLE 1

|         | Example 5 | Example 6 | Comparative example 7 | Comparative example 8 |
|---------|-----------|-----------|-----------------------|-----------------------|
| TON(Pd) | 2.8 (3 h) | 3.0 (14 h)| 3.4 (3 h)             | 2.7 (14 h)            |
| TON(Cu) | 2.8 (3 h) | 3.0 (14 h)| —                     | —                     |
| TON(Co) | —         | —         | 0.5 (3 h)             | 0.4 (14 h)            |

The TONs based on palladium and cobalt decrease in the comparative examples at an increased reaction time. Comparison of the bimetallic catalyst as per example 5 and the corresponding comparative examples 7 and 8 demonstrates a higher stability of the bimetallic catalyst of the invention compared to catalysts from the prior art.

The TON based on the cocatalyst is lower in comparative examples 7 and 8 than when using the bimetallic catalyst of the invention as per examples 5 and 6.

The invention claimed is:

1. A compound of formula (3)

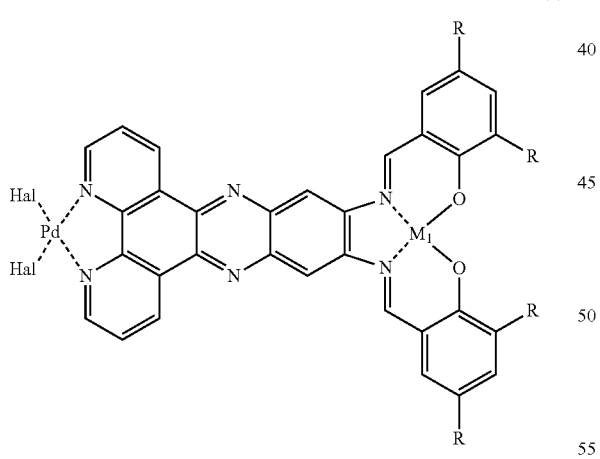

(3)

wherein
R is hydrogen, fluorine, chlorine, a nitro group, a $C_1$-$C_{22}$-alkyl radical, or a $C_6$-$C_{22}$-aryl radical;
Hal is selected from the group consisting of chloride, bromide, iodide, alkoxide, triflate, tosylate, mesylate, tetrafluoroborate, perchlorate, and hexafluorophosphate; and
$M_1$ is copper, manganese, or cobalt.

2. A process for preparing the compound of claim 1 comprising (1) hydrogenating the nitro groups of a compound of formula (4a) to form a compound of formula (4b);

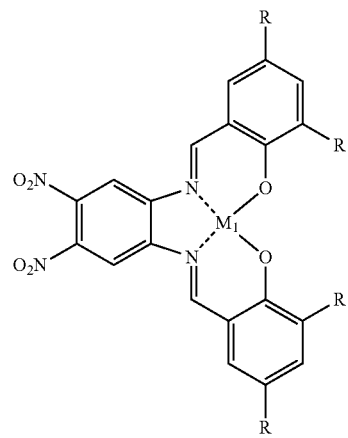

(4a)

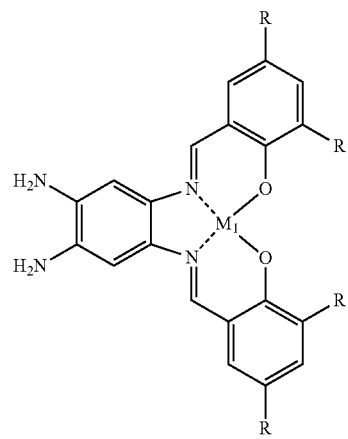

(4b)

(2) subsequently reacting the compound of formula (4b) with the phendione of formula (5)

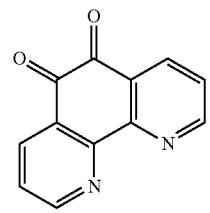

(5)

to form a ligand of formula (6)
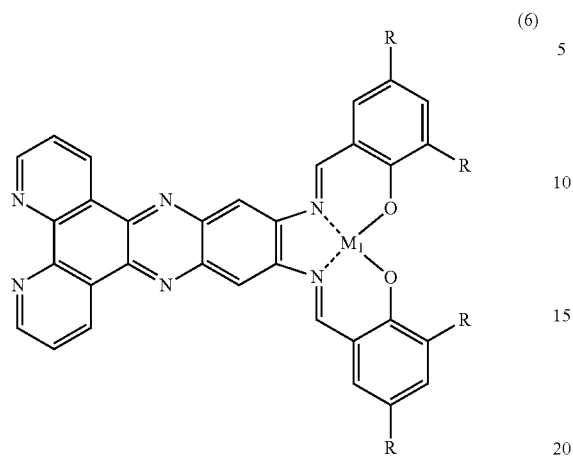
and (3) complexing the compound of formula (6) with a compound of formula (7)
$$PdHal_2L_2 \quad (7)$$
wherein
Hal is as defined above; and
L is a ligand which is optionally present.
\* \* \* \* \*